United States Patent
Kamee et al.

(10) Patent No.: US 9,423,103 B2
(45) Date of Patent: Aug. 23, 2016

(54) LIGHT SOURCE DEVICE FOR TUBULAR OBSERVATION DEVICE

(71) Applicant: OLYMPUS CORPORATION, Tokyo (JP)

(72) Inventors: Hiroyuki Kamee, Koganei (JP); Eiji Yamamoto, Musashimurayama (JP); Takeshi Ito, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/332,762

(22) Filed: Jul. 16, 2014

(65) Prior Publication Data

US 2014/0328047 A1 Nov. 6, 2014

Related U.S. Application Data

(63) Continuation of application No. PCT/JP2013/050831, filed on Jan. 17, 2013.

(30) Foreign Application Priority Data

Jan. 23, 2012 (JP) ................. 2012-010882

(51) Int. Cl.
| | |
|---|---|
| *F21V 5/00* | (2015.01) |
| *F21V 9/08* | (2006.01) |
| *G02B 23/26* | (2006.01) |
| *A61B 1/06* | (2006.01) |
| *F21V 13/08* | (2006.01) |

(52) U.S. Cl.
CPC ............... *F21V 9/08* (2013.01); *A61B 1/0684* (2013.01); *F21V 13/08* (2013.01); *G02B 23/26* (2013.01)

(58) Field of Classification Search
CPC G02B 6/0026; G02B 27/142; G02B 6/4215; G02B 6/0003; G02B 2207/113
USPC ........................................................ 362/583
See application file for complete search history.

(56) References Cited

U.S. PATENT DOCUMENTS

| | | | |
|---|---|---|---|
| 2008/0089089 A1* | 4/2008 | Hama | ................ A61B 1/0653 362/574 |
| 2010/0254153 A1 | 10/2010 | Hama et al. | |
| 2011/0077465 A1* | 3/2011 | Mizuyoshi | ......... A61B 1/00096 600/180 |

FOREIGN PATENT DOCUMENTS

| | | |
|---|---|---|
| JP | 2003-260029 A | 9/2003 |
| JP | 2006-130002 A | 5/2006 |
| JP | 2006-173324 A | 6/2006 |
| JP | 2011-147757 A | 8/2011 |
| WO | 2006/038502 A1 | 4/2006 |

OTHER PUBLICATIONS

International Preliminary Report on Patentability with the Written Opinion dated Aug. 7, 2014 received in related International Application No. PCT/JP2013/050831, together with an English language translation dated Apr. 2, 2013.
International Search Report dated Apr. 2, 2013 issued in PCT/JP2013/050831.
Japanese Office Action dated Dec. 22, 2015 from related Japanese Patent Application No. 2012-010882, together with an English language translation.

* cited by examiner

*Primary Examiner* — William Carter
(74) *Attorney, Agent, or Firm* — Scully, Scott, Murphy & Presser, P.C.

(57) ABSTRACT

A light source device includes a primary light source unit and a light converting unit. The primary light source unit includes a primary light emitting portion. The light converting unit includes a light converting member and a secondary light emitting portion. In the two-dimensional shape of the secondary light emitting portion projected on a surface perpendicular to the optical axis of primary light, the length of the minimum width of the two-dimensional shape passing through the center of gravity of the two-dimensional shape is different from the length of the maximum width of the two-dimensional shape passing through the center of gravity.

27 Claims, 16 Drawing Sheets

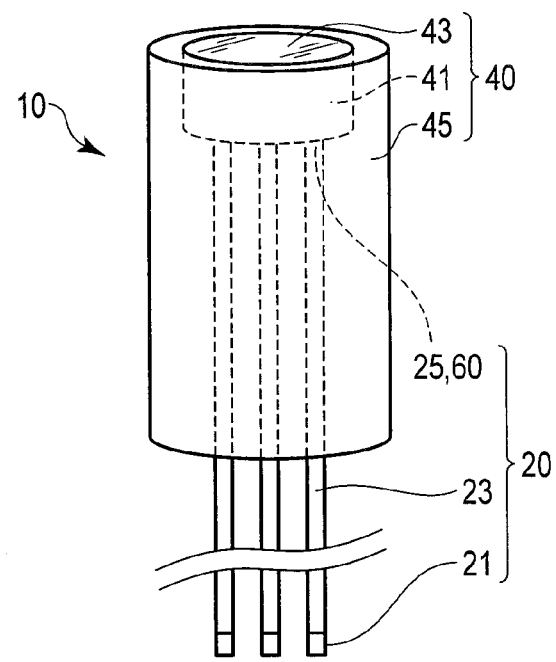
F I G. 1A
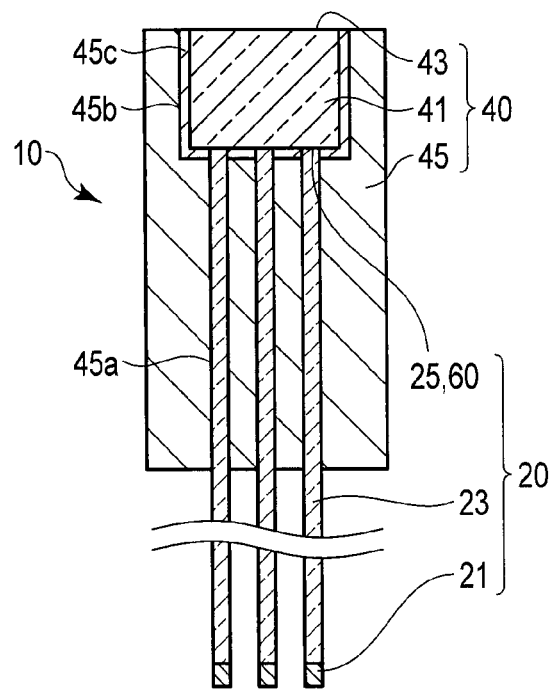
F I G. 1B

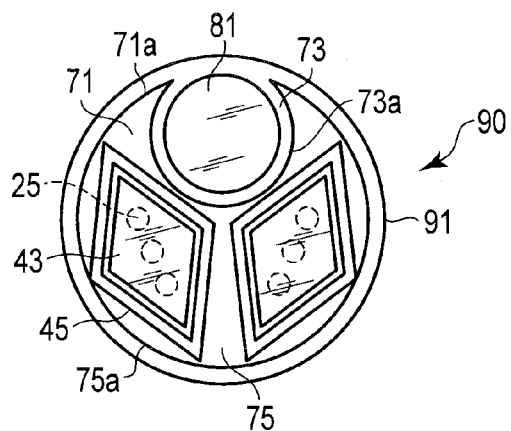
F I G. 2G
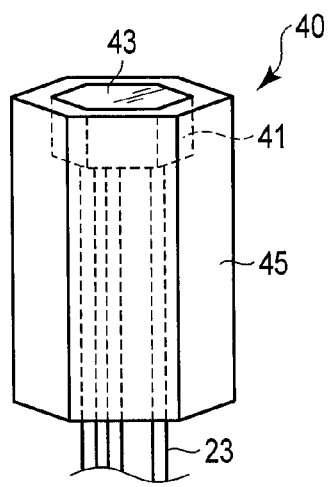
F I G. 2H
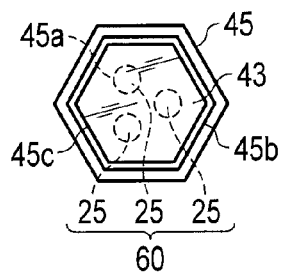
F I G. 2I

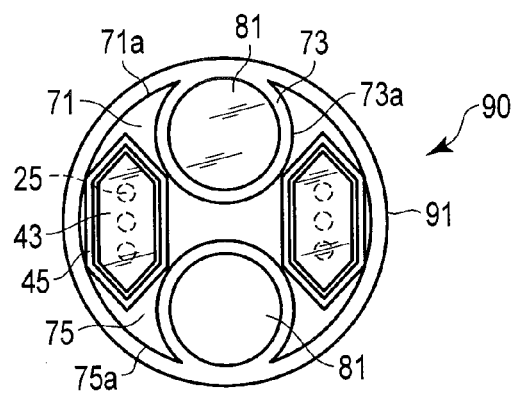
F I G. 2J
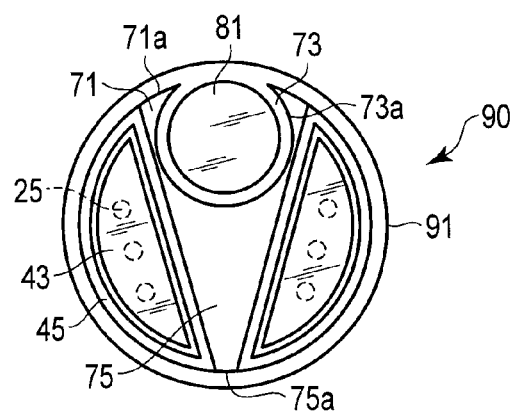
F I G. 2K
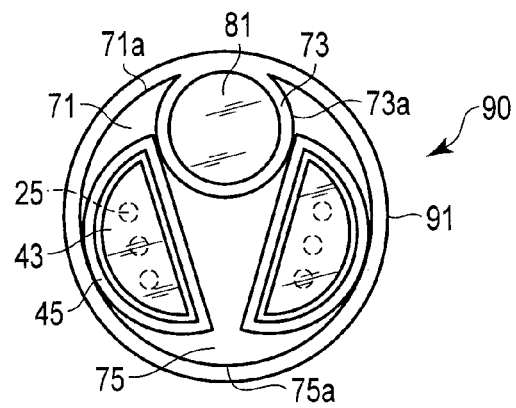
F I G. 2L

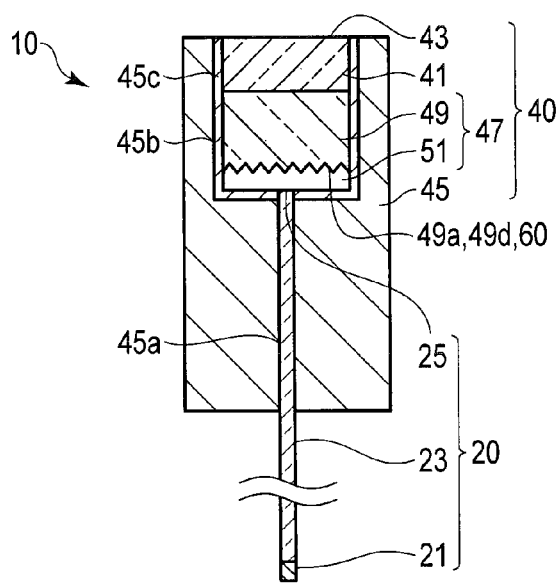
F I G. 5B
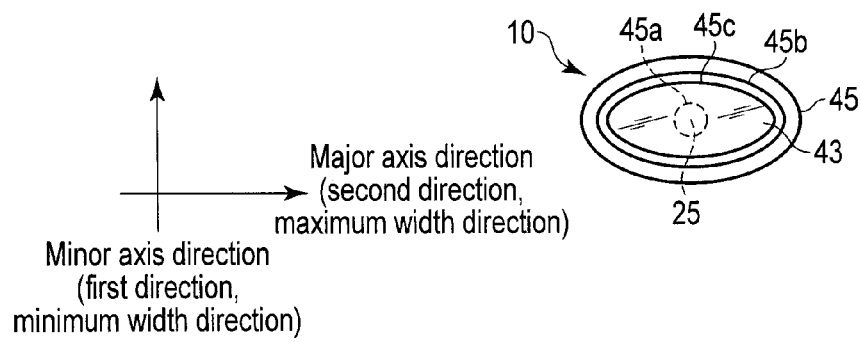
F I G. 5C
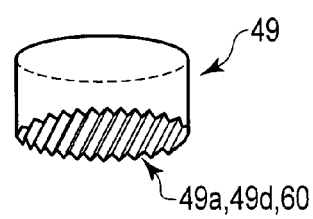
F I G. 5D

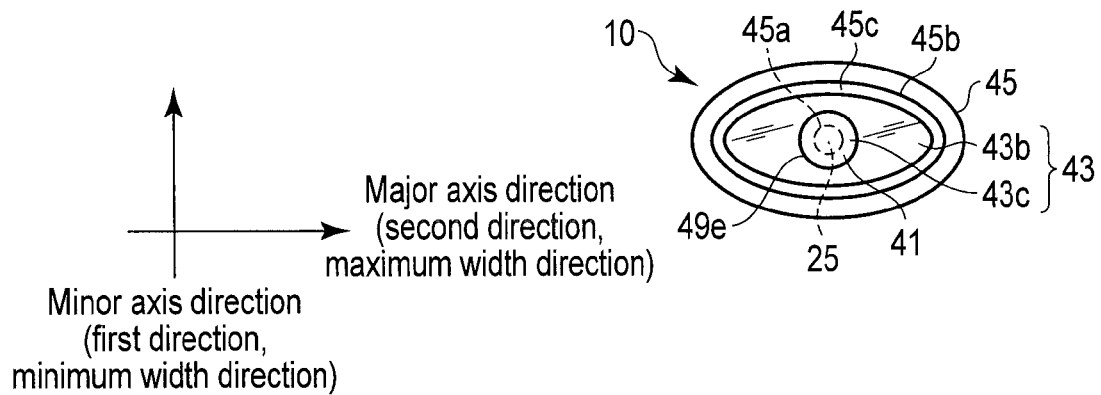
F I G. 6C
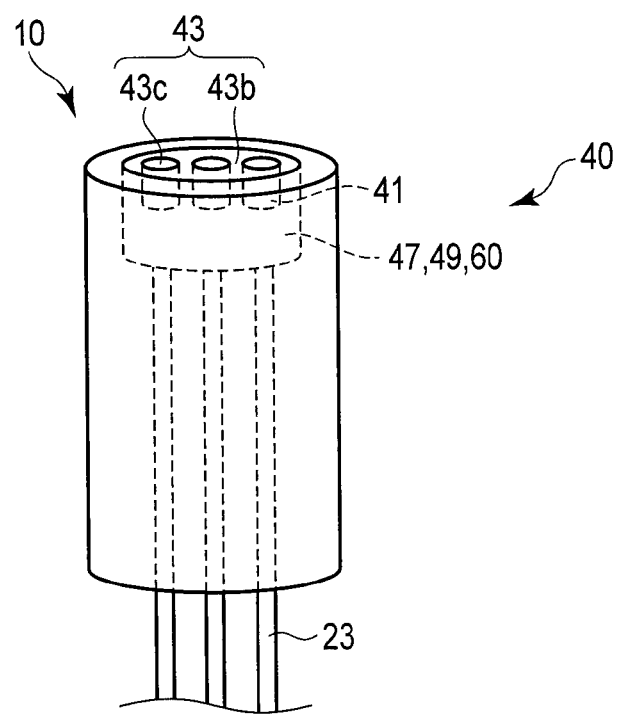
F I G. 6D

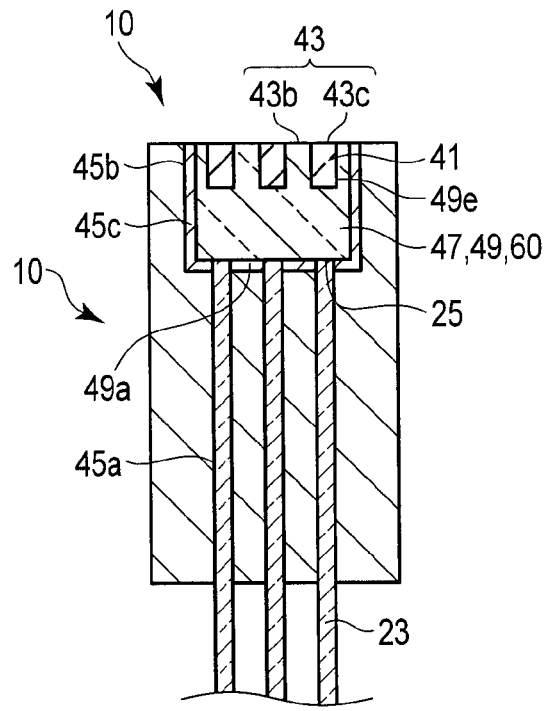
F I G. 6E
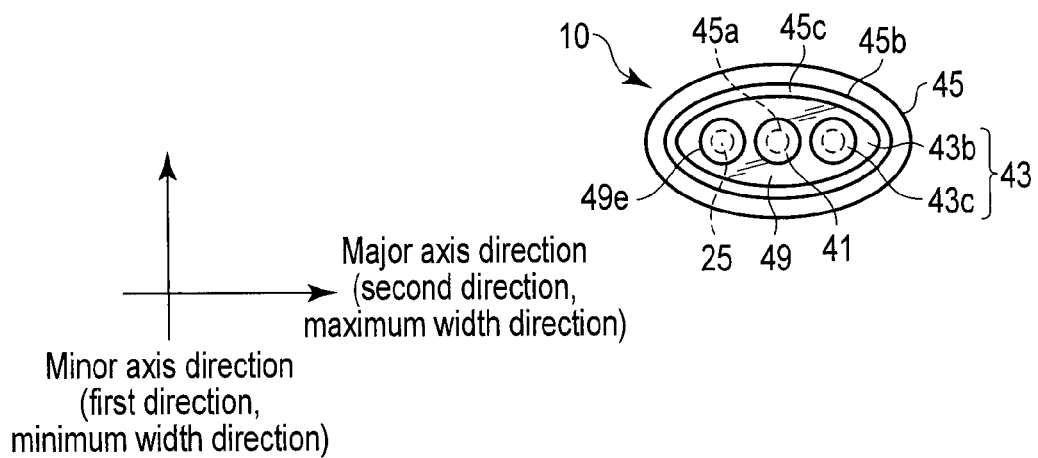
F I G. 6F

General Art

General Art

LIGHT SOURCE DEVICE FOR TUBULAR OBSERVATION DEVICE

CROSS-REFERENCE TO RELATED APPLICATIONS

This application is a Continuation application of PCT Application No. PCT/JP2013/050831, filed Jan. 17, 2013 and based upon and claiming the benefit of priority from prior Japanese Patent Application No. 2012-010882, filed Jan. 23, 2012, the entire contents of all of which are incorporated herein by reference.

BACKGROUND OF THE INVENTION

1. Field of the Invention

The present invention relates to a light source device with a high layout efficiency.

2. Description of the Related Art

Recently, space saving, lower power consumption, and higher luminance have been required for thin tubular light sources, and development thereof has been under way. Such a light source is disclosed in, for example, Jpn. Pat. Appln. KOKAI Publication No. 2006-173324.

In Jpn. Pat. Appln. KOKAI Publication No. 2006-173324, a high-performance light source device satisfies both high color rendering properties and high luminous efficiency that are in a trade-off relation.

This light source device includes a first semiconductor laser light source, a wavelength converting member, at least one first unit having a light guide, a second semiconductor laser light source, and at least one second unit having a wavelength converting member and a light guide.

The first semiconductor laser light source has a laser element which emits primary light of a blue wavelength region.

The wavelength converting member has one or more kinds of fluorescent substances. The fluorescent substance absorbs the primary light emitted from the first semiconductor laser light source, converts the wavelength thereof, and radiates light having a wavelength region longer than that of the primary light. This wavelength converting member functions as an illumination unit.

In the section of the light guide, the refractive index in the center is higher than the refractive index in the peripheral portion. The light guide guides the primary light emitted from the first semiconductor laser light source to the wavelength converting member.

The second semiconductor laser light source emits primary light having a wavelength region shorter than that of the primary light that the laser element emitted.

This light source device is provided in a tubular observation device, and the illumination unit is mounted at the distal end portion of the tubular observation device together with a second functional unit. The second functional unit has, for example, an imaging unit and an opening portion. This opening portion is provided, for example, to insert an optional member through the distal end portion. The tubular observation device is, for example, an endoscope.

FIG. 7A and FIG. 7B show front views of a distal end portion 191 (case) of a general tubular device 190. As shown in FIG. 7A, for example, the distal end face of one functional unit 181 and two illumination units 143 are provided in a distal end face 171 of the distal end portion 191. As shown in FIG. 7B, for example, the distal end faces of two functional units 181 and two illumination units 143 are provided in a distal end face 171 of the distal end portion 191. The functional units 181 are, for example, an imaging unit and an opening portion.

In general, a distal end portion of the light guide has a circular shape. In general, the illumination unit 143 has a cylinder shape. Therefor primary light is emitted from the light guide in circular shape.

As shown in FIG. 7A and FIG. 7B, in general, the distal end portion 191 has a cylinder shape and the distal end face 171 has a circular shape for matching to emitting shape of primary light. As shown in FIG. 7A and FIG. 7B, in general, the distal end face 171 has a circular shape, the distal end portion 191 has a cylinder shape.

As shown in FIG. 7A and FIG. 7B, when the functional units 181 and the illumination unit 143 are provided adjacent to one another, a fill factor in the distal end portion 191 including distal end face 171 is decreased, a dead space is formed. That is, wasteful space is occurred and layout efficiency is decreased in the distal end portion 191 including distal end face 171.

The present invention has been made under these circumstances, and an object of the invention is to provide a light source device which the formation of dead space is suppressed, wasteful space is eliminated, and layout efficiency is increased in the part in which the light source device is provided.

BRIEF SUMMARY OF THE INVENTION

An aspect of a light source device of the present invention includes a primary light source unit and a light converting unit, the primary light source unit includes a primary light emitting portion which emits primary light, the light converting unit includes a light converting member which converts the optical properties of the primary light when the primary light is applied thereto and which generates secondary light different from the primary light, and a secondary light emitting portion which emits the secondary light generated by the light converting member, wherein in the two-dimensional shape of the secondary light emitting portion projected on a surface perpendicular to the optical axis of the primary light, the length of the minimum width of the two-dimensional shape passing through the center of gravity of the two-dimensional shape is different from the length of the maximum width of the two-dimensional shape passing through the center of gravity.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1A is a schematic perspective view of a light source device according to a first embodiment of the present invention;

FIG. 1B is a longitudinal sectional view of the light source device shown in FIG. 1A;

FIG. 2G is a diagram showing a layout plane in which holding members having a rhomboidal-prism shape are provided;

FIG. 2H is a perspective view of a holding member having a hexagonal-prism shape;

FIG. 2I is a front view of the holding member shown in FIG. 2H;

FIG. 2J is a diagram showing a layout plane in which the holding members shown in FIG. 2H are provided;

FIG. 2K is a diagram showing a layout plane in which holding members having a semicircular-cylinder shape are provided;

FIG. 2L is a diagram showing a layout plane in which holding members having a semicircular-cylinder shape are provided;

FIG. 5B is a longitudinal sectional view of the light source device shown in FIG. 5A;

FIG. 5C is a front view of the light source device shown in FIG. 5A;

FIG. 5D is a perspective view of a transparent member shown in FIG. 5A;

FIG. 6C is a front view of the light source device shown in FIG. 6A;

FIG. 6D is a schematic perspective view of the light source device shown in FIG. 6A having more than one optical fiber, primary light emitting portions, and light converting members;

FIG. 6E is a longitudinal sectional view of the light source device shown in FIG. 6D;

FIG. 6F is a front view of the light source device shown in FIG. 6D;

DETAILED DESCRIPTION OF THE INVENTION

Figure 1C:
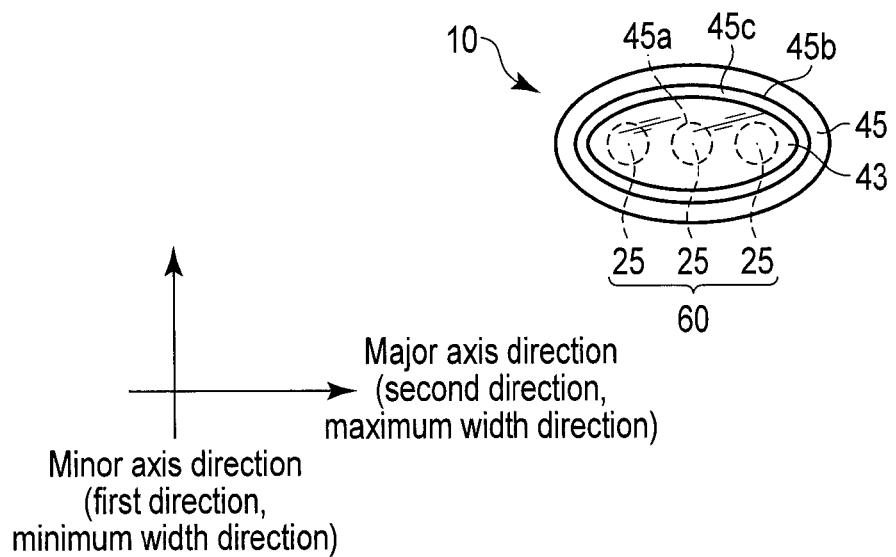
FIG. 1C is a front view of the light source device shown in FIG. 1A.

Hereinafter, embodiments of the present invention will be described in detail with reference to the drawings.

For purposes of this Application, the term "trace" is defined as offset and/or parallel and/or coincident.

The first embodiment is described with reference to FIG. 1A, FIG. 1B, FIG. 1C, FIG. 1D, FIG. 1E, and FIG. 1F.

Hereinafter, in the traveling direction of primary light, the direction in which the primary light is emitted from a primary light emitting portion 25, the front side in the traveling direction of primary light, and the side of a secondary light emitting portion 43 are referred to as forward. Moreover, in the traveling direction of primary light, the rear side in the traveling direction of primary light, and the side of a primary light source 21 are referred to as rearward. An axis on which the primary light is emitted from the center of the primary light emitting portion 25 is referred to as an optical axis. The distal end face (front surface) of a distal end portion 91 of a tubular device 90 is referred to as a layout plane 71.

As a reflecting portion 45c is not shown in FIG. 1A, some components are not shown in some of the drawings for simplicity.

As shown in FIG. 1A and FIG. 1B, a light source device 10 includes a primary light source unit 20 and a light converting unit 40.

As shown in FIG. 1A and FIG. 1B, the primary light source unit 20 has the primary light sources 21 which emit primary light such as excitation light, optical fibers 23 serving as light guide members which guide the primary light emitted from the primary light sources 21 to the light converting unit 40, and the primary light emitting portions 25 which are provided at the end portions of the optical fibers 23 and which emit the primary light guided by the optical fiber 23 to the light converting unit 40.

As shown in FIG. 1A and FIG. 1B, the primary light sources 21 are, for example, point light sources having the following characteristics: emitting primary light having a straight traveling property, being high in the incidence efficiency of the primary light into the optical fibers 23, being high in the efficiency of energy use, being low in power consumption, and being small in size. The primary light source 21 emits the primary light which causes excitation and light generation in a light converting member 41 of the light converting unit 40. This primary light source 21 has, for example, a semiconductor laser light source or an LED. The primary light source 21 is optically connected to the optical fiber 23 via an unshown lens.

As shown in FIG. 1B, for example, three primary light sources 21 are provided. These primary light sources 21 are provided adjacent to one another, apart from one another, and linearly beside one another in a direction that intersects at right angles with the optical axis.

As shown in FIG. 1A and FIG. 1B, the optical fiber 23 has, for example, a flexible circular-cylinder shape. The same number of optical fibers 23 as the primary light sources 21, for example, three optical fibers 23 are provided. One end portion of one optical fiber 23 is optically connected to one primary light source 21. These optical fibers 23 are provided adjacent to one another, apart from one another, and beside one another.

The optical fiber 23 has the property of efficiently guiding primary light. The optical fiber 23 is made of, for example, glass or plastics. The optical fiber 23 has, for example, a multifiber mode optical fiber. The optical fiber 23 has optical properties which allow the primary light to be highly efficiently guided forward so that the primary light is emitted forward from the primary light emitting portions 25 without any great energy loss. In this instance, the emission angle of the primary light is determined by the NA of the optical fiber 23 and the refractive index of the light converting member 41.

As shown in FIG. 1A and FIG. 1B, one primary light emitting portion 25 is provided at the other end portion of one optical fiber 23. Therefore, the same number of primary light emitting portions 25 as the optical fibers 23, for example, three primary light emitting portions 25 are provided. The primary light emitting portion 25 is an emission surface to emit the primary light, and is the end face of the optical fiber 23. The primary light emitting portion 25 has the same shape as, for example, the other end portion of one optical fiber 23, and has, for example, a circular shape. Therefore, a beam spot formed by the primary light emitted from one primary light emitting portion 25 has a circular shape.

In this instance, the beam spot shows an irradiation region of the primary light projected on a surface perpendicular to the optical axis. The beam spot is defined as a region which is irradiated at an intensity higher than at least $1/e^2$ of the maximum intensity of the primary light. e is Napier's constant as a base of a natural logarithm.

According to the present embodiment, as shown in FIG. 1B and FIG. 1C, the optical fibers 23 are provided adjacent to one another, apart from one another, and beside one another along the direction (maximum width direction) that intersects at right angles with the optical axis, as described above. Therefore, the primary light emitting portions 25 are provided in a similar manner as the optical fibers 23. Thus, the beam spot formed by the primary light emitted from all three primary light emitting portions 25 does not have a circular shape. In this case, the beam spot has a shape in which circles are provided beside one another along the direction that intersects at right angles with the optical axis so that the edge of one circle is located in contact with or apart from the edge of another circle. Alternatively, the beam spot has a shape in which circles are provided beside one another along the direction that intersects at right angles with the optical axis so that a part of one circle overlaps a part of another adjacent circle.

The shape of the beam spot is then converted by the arrangement of the primary light emitting portions 25 so that, for example, the shape of the beam spot in a first direction is shorter and the shape of the beam spot in a second direction is longer. As shown in FIG. 1C, the first direction represents, for example, the direction that intersects at right angles with the optical axis, and represents a later-described minimum width direction of the secondary light emitting portion 43. As shown in FIG. 1C, the second direction represents, for example, the direction that intersects at right angles with the optical axis and the first direction, and represents a later-described maximum width direction of the secondary light emitting portion 43. Thus, the light source device 10 further includes a shape converting unit 60 which converts, to a desired shape, the shape of the beam spot of the primary light emitted from the primary light emitting portions 25 and projected on the bottom surface of the light converting member 41. As shown in FIG. 1C, the primary light emitting portions 25 function as the shape converting unit 60.

As shown in FIG. 1A and FIG. 1B, the light converting unit 40 has the light converting member 41 which converts the optical properties of the primary light when the primary light is applied thereto and which generates secondary light different from the primary light, the secondary light emitting portion 43 which is provided in the light converting member 41 and which emits the secondary light, and a holding member 45 which holds the light converting member 41 and the optical fibers 23.

The light converting member 41 absorbs the primary light, and then converts the wavelength of the absorbed primary light to a wavelength different from that of the primary light to generate the secondary light having this wavelength. Thus, the light converting member 41 is a wavelength converting member which converts the wavelength of the primary light, and is an optical element which functions when the primary light is applied thereto. The light converting member 41 has, for example, a fluorescent material. When the secondary light emitting portion 43 emits, for example, white illumination light as the secondary light, the secondary light emitting portion 43 is formed by several kinds of powder fluorescent materials and a transparent resin. In this instance, several kinds of powder fluorescent materials are in combination with one another and dispersed into the resin, and the resin is solidified in this state so that the light converting member 41 is shaped.

As shown in FIG. 1A, the light converting member 41 has, for example, an elliptic-cylinder shape. The light converting member 41 has thickness and concentration that can sufficiently absorb the primary light emitted from the primary light emitting portions 25. The bottom surface of the light converting member 41 has an elliptic shape. As shown in FIG. 1A and FIG. 1B, the area of this bottom surface is larger than the area of the minimum ellipse covering all the primary light emitting portions 25. In the center of the bottom surface, the circumference of the center including the center of the bottom surface is in abutment with the primary light emitting portions 25. The minor axis direction (minimum width direction) of the light converting member 41 including the bottom surface represents the first direction shown in FIG. 1C, and is provided along the direction that intersects at right angles with the optical axis. The major axis direction (maximum width direction) of the light converting member 41 including the bottom surface represents the second direction shown in FIG. 1C, and is provided along a direction in which the optical fibers 23 (primary light emitting portions 25) are provided beside one another, that is, a direction that intersects at right angles with the optical axis direction and the minor axis direction.

The secondary light emitting portion 43 shown in FIG. 1A and FIG. 1B is also an illumination unit which illuminates an imaging target with the secondary light. Therefore, the secondary light emitting portion 43 is also provided in the forefront of the light converting member 41. The secondary light emitting portion 43 is provided along the surface perpendicular to the optical axis. The secondary light emitting portion 43 is formed as a plane. This secondary light emitting portion 43 functions as, for example, the upper surface of the light converting member 41. Thus, as shown in FIG. 1C, the secondary light emitting portion 43 has, for example, an elliptic shape. As shown in FIG. 1C, as regards the shape of the secondary light emitting portion 43, the length of the minimum width of the secondary light emitting portion 43 passing through the center of gravity of the secondary light emitting portion 43 is different from the length of the maximum width of the secondary light emitting portion 43 passing through the center of gravity of the secondary light emitting portion 43. This minimum width represents, for example, the minimum length in the distance (length) from the edge of the secondary light emitting portion 43 to the opposite edge passing through the center of gravity of the secondary light emitting portion 43. The maximum width represents, for example, the maximum length in the distance (length) from the edge of the secondary light emitting portion 43 to the opposite edge passing through the center of gravity of the secondary light emitting portion 43. In this instance, as shown in FIG. 1C, the minor axis direction (minimum width direction) of the secondary light emitting portion 43 represents the first direction, and is a direction that intersects at right angles with the optical axis. The major axis direction (maximum width direction) of the secondary light emitting portion 43 represents the second direction as shown in FIG. 1C, and is a direction in which the optical fibers 23 (primary light emitting portions 25) are provided beside one another.

To sum up, it is represented that, as regards the two-dimensional shape of the secondary light emitting portion 43 projected on the surface perpendicular to the optical axis of the primary light, the length of the minimum width of the two-dimensional shape passing through the center of gravity of the two-dimensional shape is different from the length of the maximum width of the two-dimensional shape passing through the center of gravity.

The holding member 45 shown in FIG. 1A and FIG. 1B is made of at least one of, for example, zirconia, glass, and a metal. This metal is made of at least one of, for example, nickel, SUS, and brass. The holding member 45 has, for example, an elliptic shape.

Figure 1D:
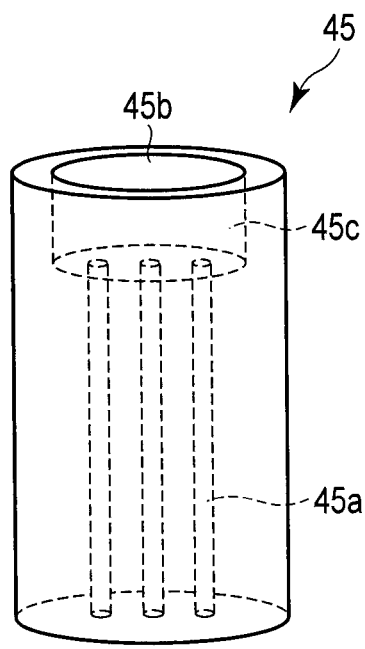
FIG. 1D is a perspective view of a holding member shown in FIG. 1A.

As shown in FIG. 1D, the holding member 45 has therein rear holding hole portions 45a which hold the optical fibers 23, and a front holding hole portion 45b which holds the light converting member 41. The rear holding hole portions 45a are provided in the rear of the front holding hole portion 45b in the axial direction of the holding member 45. The rear holding hole portions 45a are exposed to the outside in the rear part of the holding member 45, and the front holding hole portion 45b is exposed to the outside in the front part of the holding member 45. The rear holding hole portions 45a are in communication with the bottom surface of the front holding hole portion 45b.

As shown in FIG. 1D, the same number of rear holding hole portions 45a as the optical fibers 23, for example, three rear holding hole portions 45a are provided. As shown in FIG. 1A and FIG. 1B, one optical fiber 23 is provided in one rear holding hole portion 45a. The rear holding hole portion 45a has the same shape as the optical fiber 23, for example, a circular-cylinder shape, and has the same size as the optical fiber 23. The optical fibers 23 are fitted to or adhesively bonded to the rear holding hole portions 45a. These rear holding hole portions 45a are provided parallel to one another along the optical axis. As shown in FIG. 1C, the rear holding hole portions 45a are provided adjacent to one another, apart from one another, and linearly beside one another along the second direction.

As shown in FIG. 1D, one front holding hole portion 45b is provided. As shown in FIG. 1A and FIG. 1B, the front holding hole portion 45b has the same shape as the light converting member 41, for example, a circular-cylinder shape. Thus, the outside diameter and height of the front holding hole portion 45b are substantially the same as the outside diameter and height of the light converting member 41. The volume of the front holding hole portion 45b is substantially the same as the volume of the light converting member 41. The light converting member 41 is fitted to or adhesively bonded to the front holding hole portion 45b. The front holding hole portion 45b is larger than the area of the minimum ellipse covering all the primary light emitting portions 25.

In the front holding hole portion 45b having the elliptic-cylinder shape, the minor axis direction (minimum width direction) of the front holding hole portion 45b represents the first direction as shown in FIG. 1C, and is provided along the direction that intersects at right angles with the optical axis. The major axis direction (maximum width direction) of the front holding hole portion 45b represents the second direction as shown in FIG. 1C, and is provided along the direction in which the optical fibers 23 (primary light emitting portions 25) are provided beside one another.

The distal end face (front surface) of the holding member 45 in which the front holding hole portion 45b is provided has a hollow elliptic shape. The size of the outer shape of this distal end face is larger than the size of the secondary light emitting portion 43, and is similar to the size of the secondary light emitting portion 43.

As shown in FIG. 1C, the front holding hole portion 45b has the reflecting portion 45c which is provided on the inner circumferential surface and bottom surface of the front holding hole portion 45b and which highly efficiently reflects the primary light and the secondary light. The reflecting portion 45c is made of a material having a function to reflect visible light. This material represents, for example, silver or aluminum. The reflecting portion 45c is provided on the inner circumferential surface and bottom surface of the front holding hole portion 45b by, for example, a plating method, a vapor deposition method, or a sputtering method. Because of the general optical properties of the light converting member 41, the reflecting portion 45c reflects forward the secondary light which has been emitted from the secondary light emitting portion 43 in all directions.

As shown in FIG. 1B, the holding member 45 directly holds therein the optical fibers 23 and the light converting member 41 by the rear holding hole portions 45a and the front holding hole portion 45b so that the optical fibers 23 and the light converting member 41 are optically coupled to each other inside the holding member 45. The optical fibers 23 which are fitted to or adhesively bonded to the rear holding hole portions 45a and the light converting member 41 which is fitted to or adhesively bonded to the front holding hole portion 45b are in direct abutment with each other inside the holding member 45. More specifically, the primary light emitting portion 25 and the bottom surface of the light converting member 41 are in abutment with each other.

Figure 1E:
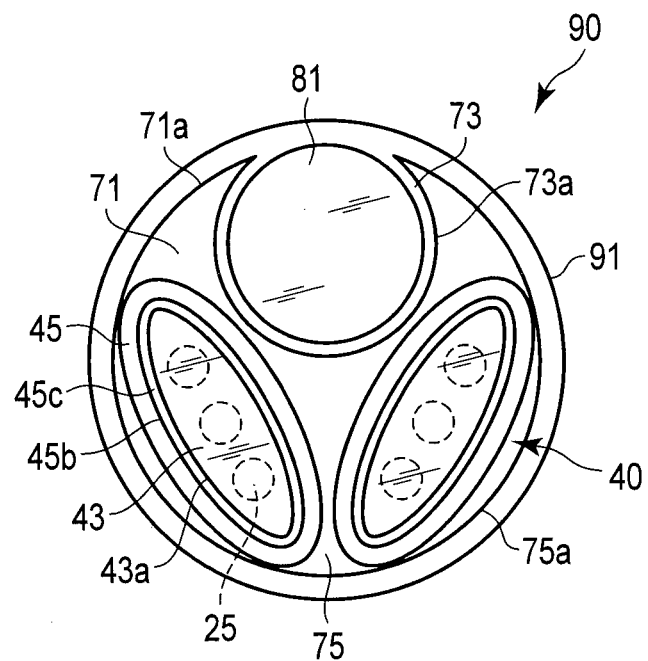
FIG. 1E is a diagram showing a layout plane in which an illumination unit and an imaging unit are provided.

As shown in FIG. 1E, this light converting unit 40 is incorporated in the distal end portion 91 of the tubular device 90 together with at least one functional unit 81. The functional unit 81 has, for example, an imaging unit and an opening portion. The distal end portion 91 has, for example, a circular-cylinder shape, and is a case. The layout plane 71 which is the distal end face of the distal end portion 91 has, for example, a circular shape. In this case, the light converting unit 40 is embedded in the distal end portion 91 so that the secondary light emitting portion 43 and the distal end face of the holding member 45 are provided in the layout plane 71 and so that the secondary light emitting portion 43 and the distal end face of the holding member 45 are exposed to the outside. The functional units 81 are embedded in the distal end portion 91 so that the distal end faces of all the functional units 81 are provided in the layout plane 71 and so that the distal end faces of the functional units 81 are exposed to the outside.

In this instance, at least part of an outline 43a of the two-dimensional shape of the secondary light emitting portion 43 traces an edge 71a of the layout plane 71. This two-dimensional shape represents a shape formed when the secondary light emitting portion 43 is projected on the surface perpendicular to the optical axis of the primary light. That is, at least part of the outline 43a of the secondary light emitting portion 43 traces the edge 71a of the layout plane 71. In other words, at least part of the outline 43a is offset relative to the edge 71a of the layout plane 71. In other words again, at least part of the outline 43a is parallel to the edge 71a of the layout plane 71, and extends along the edge 71a of the layout plane 71.

Figure 1F:
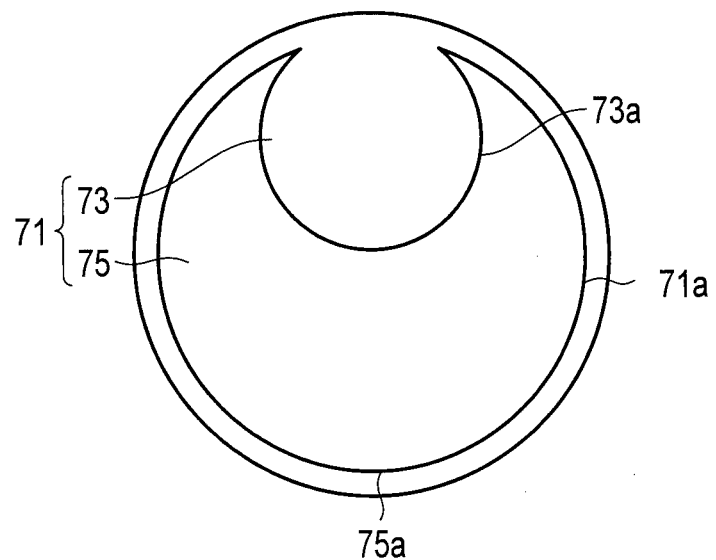
FIG. 1F is a diagram illustrating a layout plane, a region in which distal end portion surfaces of all functional units are disposed, and a layout possible region.

As shown in FIG. 1F, the layout plane 71 has a region 73 in which the distal end faces of all the functional units 81 are disposed, and a layout possible region 75 representing a region in which the region 73 is removed from the layout plane 71. In other words, the layout possible region 75 represents a region in which the secondary light emitting portion 43 can be disposed in the layout plane 71. Therefore, the layout possible region 75 is surrounded by the edge 71a of the layout plane 71 and an edge 73a of the region 73. In this instance, part of an edge 75a of the layout possible region 75 has, for example, an arc shape.

The secondary light emitting portion 43 is provided in the layout possible region 75 so that The secondary light emitting portion 43 is exposed to the outside. At least part of the outline 43a of the two-dimensional shape has a shape that traces part of the edge 75a of the layout possible region 75, and has, for example, an elliptic shape. More specifically, at least part of the outline 43a of the secondary light emitting portion 43 traces the edge 75a of the layout possible region 75, and has an elliptic shape.

Although at least part of the outline 43a of the secondary light emitting portion 43 traces the edge 71a of the layout plane 71, the present invention does not need to be limited to this. For example, at least part of the outline of the distal end face of the holding member 45 or at least part of the outline of the holding member 45 may trace the edge 71a of the layout plane 71.

Now, an operation method according to the present embodiment is described.

Primary light is emitted from the primary light source 21, guided to the primary light emitting portions 25 by the optical fiber 23, and emitted toward the light converting member 41 by the primary light emitting portions 25. The shape of the beam spot of the primary light emitted from the three primary light emitting portions 25 is converted to correspond to the shape of the secondary light emitting portion 43 by the arrangement of the primary light emitting portions 25, i.e., by the shape converting unit 60. In this state, the primary light incidents the light converting member 41, and is converted to secondary light by the light converting member 41. The secondary light travels through the light converting member 41. In this instance, some of the secondary light travels toward the reflecting portion 45c, is reflected forward by the reflecting portion 45c, and is emitted to the outside from the secondary light emitting portion 43. The rest of the secondary light directly travels to the secondary light emitting portion 43, and is emitted to the outside from the secondary light emitting portion 43.

Figure 7A:
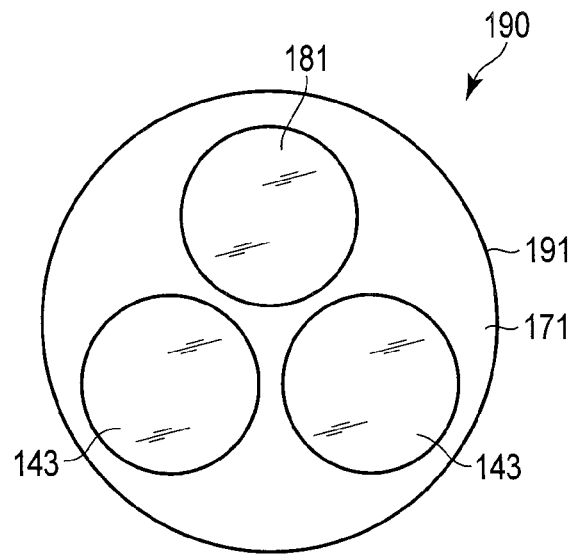
FIG. 7A shows a layout plane (front view) of the distal end portion of a general tubular observation device.
Figure 7B:
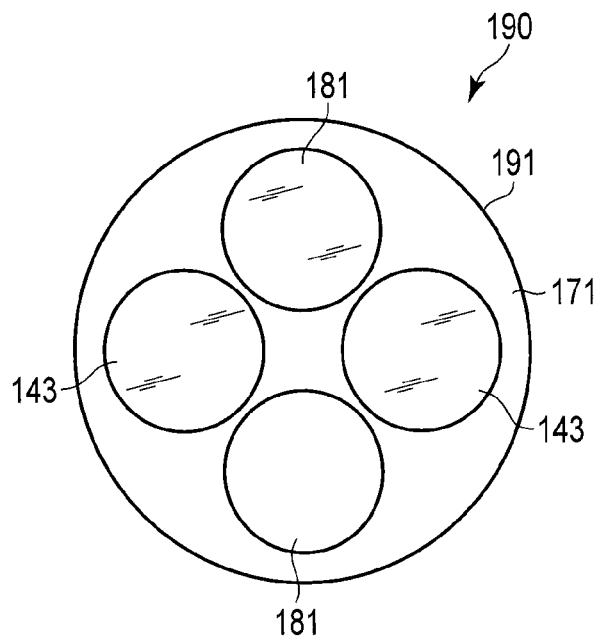
FIG. 7B shows a layout plane (front view) of the distal end portion of a general tubular observation device.

As shown in FIG. 1C and FIG. 1D, the secondary light emitting portion 43 has, for example, an elliptic shape, and at least part of the outline 43a of the secondary light emitting portion 43 traces the edge 75a of the layout possible region 75. Thus, according to the present embodiment, the formation of dead space in the layout plane 71 is suppressed, wasteful space in the layout plane 71 is eliminated, and layout efficiency is increased, as compared with the structure shown in FIG. 7A.

As shown in FIG. 1A, FIG. 1C, and FIG. 1E, the light converting member 41 and the holding member 45 have, for example, an elliptic-cylinder shape to correspond to the secondary light emitting portion 43, and at least part of the outline of the distal end face of the holding member 45 and at least part of the outline of the holding member 45 trace the edge 75a of the layout possible region 75. Thus, according to the present embodiment, the formation of dead space in the distal end portion 91 is suppressed, wasteful space in the distal end portion 91 is eliminated, and layout efficiency is increased, as compared with the structure shown in FIG. 7A.

As shown in FIG. 1B and FIG. 1C, three optical fibers 23 are provided for one light converting member 41. In this instance, the optical fibers 23 and the primary light emitting portions 25 are provided adjacent to one another, apart from one another, and beside one another along the major axis direction (maximum width direction) of the secondary light emitting portion 43. Thus, as shown in FIG. 1B and FIG. 1C, in the bottom surface of the light converting member 41 having the elliptic shape, the formation of dead space is suppressed, wasteful space is eliminated, and layout efficiency is increased. The primary light fully illuminates the light converting member 41.

The arrangement of the optical fibers 23 (primary light emitting portions 25), i.e., the shape converting unit 60 is converted so that the shape of the beam spot of the primary light corresponds to the shape of the secondary light emitting portion 43. Thus, the shape of the beam spot of the primary light is short in the minimum width direction of the secondary light emitting portion 43 and long in the maximum width direction of the secondary light emitting portion 43. In this state, the primary light illuminates the light converting member 41.

Since three optical fibers 23 are provided, the primary light is dispersed into three parts and then illuminates the light converting member 41. Thus, the places where heat is generated in the optical fibers 23 are dispersed into three places, and heat in the light source device 10 is also dispersed. As a result, the primary light fully and more strongly illuminates the light converting member 41. The secondary light is then fully and more strongly emitted.

As shown in FIG. 1B, the area of the bottom surface of the light converting member 41 is larger than the area of the minimum ellipse covering all the primary light emitting portions 25. Therefore, the primary light emitted from the three primary light emitting portions 25 illuminates the light converting member without leakage.

The reflecting portion 45c reflects the secondary light forward, and the secondary light emitting portion 43 fully emits the secondary light.

In general, when the minor axis of an ellipse has the same length as the diameter of a circle, the area of the ellipse is larger than the area of the circle. Therefore, the secondary light emitting portion 43 having an elliptic shape is larger than the secondary light emitting portion 43 having a circular shape. That is, the light emitting surface of the secondary light emitting portion 43 having an elliptic shape is larger than the light emitting surface of the secondary light emitting portion 43 having a circular shape. Thus, more secondary light is emitted. The secondary light emitting portion 43 according to the present embodiment surface-emits the secondary light to the imaging target even if the distal end face of the distal end portion 91 is close to the imaging target. Therefore, according to the present embodiment, it is possible to provide an environment in which the imaging target is uniformly illuminated.

Thus, according to the present embodiment, as shown in FIG. 1C and FIG. 1E, the secondary light emitting portion 43 has, for example, an elliptic shape, and at least part of the outline 43a of the secondary light emitting portion 43 traces the edge 75a of the layout possible region 75. Thus, according to the present embodiment, in the layout plane 71, the formation of dead space is suppressed, wasteful space is eliminated, and layout efficiency is increased, as compared with the structure shown in FIG. 7A.

According to the present embodiment, as shown in FIG. 1A, FIG. 1C, and FIG. 1E, the light converting member 41 and the holding member 45 have, for example, an elliptic-cylinder shape to correspond to the secondary light emitting portion 43, and at least part of the outline of the distal end face of the holding member 45 and at least part of the outline of the holding member 45 trace the edge 75a of the layout possible region 75. Thus, according to the present embodiment, in the distal end portion 91 representing the part in which the light converting unit 40 is provided, the formation of dead space can be suppressed, wasteful space can be eliminated, and layout efficiency can be increased, as compared with the structure shown in FIG. 7A.

According to the present embodiment, as shown in FIG. 1C, the optical fibers 23 and the primary light emitting portions 25 are provided along the major axis direction (maximum width direction) of the secondary light emitting portion 43. Thus, according to the present embodiment, in the bottom surface of the light converting member 41 having the elliptic shape, the formation of dead space can be suppressed, wasteful space can be eliminated, and layout efficiency can be increased. According to the present embodiment, the primary light can fully illuminate the light converting member 41.

According to the present embodiment, the shape converting unit 60 converts the shape of the beam spot of the primary light to correspond to the shape of the secondary light emitting portion 43. Thus, according to the present embodiment, the light converting member 41 including the secondary light emitting portion 43 can be disposed in the distal end portion 91 including the layout possible region 75 without wasting space.

According to the present embodiment, the primary light emitting portions 25 function as the shape converting unit 60. Thus, according to the present embodiment, it is not necessary to provide any new member for the shape converting unit 60, and the configuration of the light source device 10 can be simpler.

According to the present embodiment, the primary light can be applied to substantially the entire bottom surface of the light converting member 41 by the shape converting unit 60. Thus, according to the present embodiment, local heat generation can be prevented in the bottom surface of the light converting member 41, stronger primary light can be applied to the bottom surface, and bright secondary light can be emitted. According to the present embodiment, the light source device 10 that is bright can be provided.

According to the present embodiment, the secondary light emitting portion 43 has an elliptic shape. However, the shape of the secondary light emitting portion 43 is not limited to this as long as the formation of dead space can be suppressed, wasteful space can be eliminated, and layout efficiency can be increased.

For example, the two-dimensional shape has one rotation symmetry axis, and this rotation symmetry axis has only to be a twofold or more and sixfold or less rotation axis. Thus, for example, the secondary light emitting portion 43 has only to have at least one of an elliptic shape shown in FIG. 1C, a triangular shape shown in FIG. 2A, FIG. 2B, and FIG. 2C, a quadrangular shape such as a rectangle shown in FIG. 2D, FIG. 2E, and FIG. 2F, a rhombic shape shown in FIG. 2G, and a parallelogram, a pentangular shape, a hexangular shape shown in FIG. 2H, FIG. 2I, and FIG. 2J, a semicircular shape shown in FIG. 2K and FIG. 2L, and a shape at least partly having an arc or an elliptic arc as shown in FIG. 1C, FIG. 2K, and FIG. 2L.

That is, that at least part of the outline 43a traces the edge 75a of the layout possible region 75 represents that at least part of the outline 43a is configured by at least one of a curve and a straight line to trace the edge 75a. Thus, it is possible to suppress the formation of dead space between the outline 43a and the edge 75a. Accordingly, in the layout plane 71, it is possible to eliminate wasteful space, and increase layout efficiency.

It is preferable that when the secondary light emitting portion 43 has a shape having arc, the curvature of the arc is the same as the curvature of the edge 75a of the layout possible region 75.

Figure 2A:
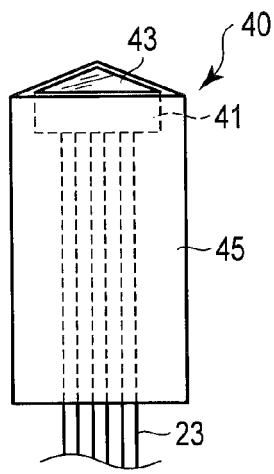
FIG. 2A is a perspective view of a holding member having a triangular-prism shape.
Figure 2B:
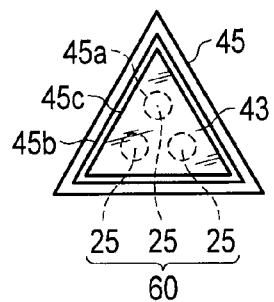
FIG. 2B is a front view of the holding member shown in FIG. 2A.
Figure 2C:
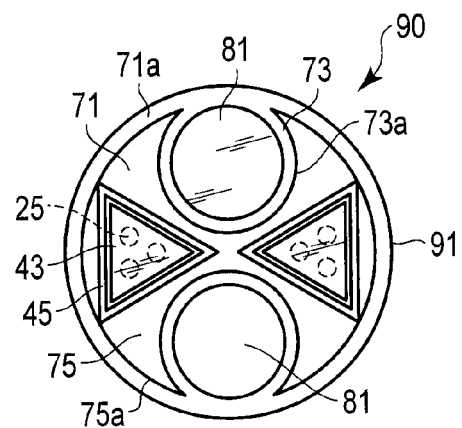
FIG. 2C is a diagram showing a layout plane in which the holding members shown in FIG. 2A are provided.
Figure 2D:
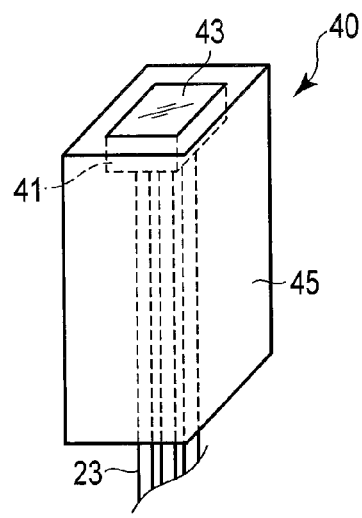
FIG. 2D is a perspective view of a holding member having a rectangular-prism shape.
Figure 2E:
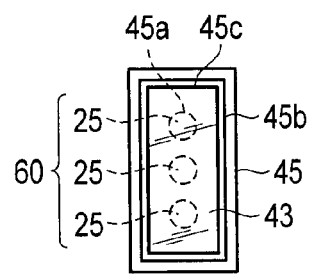
FIG. 2E is a front view of the holding member shown in FIG. 2D.
Figure 2F:
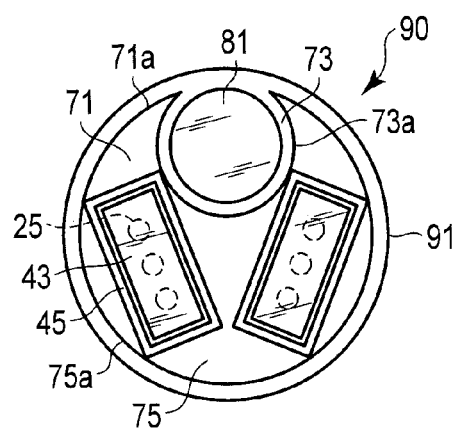
FIG. 2F is a diagram showing a layout plane in which the holding members shown in FIG. 2D are provided.

For example, when the secondary light emitting portion 43 has a polygonal shape as shown in FIG. 2A, the vertexes may be formed by curves.

The light converting member 41, the rear holding hole portions 45a, and the holding member 45 have only to have a cylindrical shape that traces the shape of the secondary light emitting portion 43.

According to the present embodiment, the light converting member 41 has, for example, a fluorescent material. However, the present invention does not need to be limited to this.

A: For example, the light converting member 41 may have at least one of a concave lens, a convex lens, a hologram lens, and a diffraction grating. The concave lens, the convex lens, and a combination of the concave lens and the convex lens function as a radiation angle conversion member which converts the radiation angle of the secondary light. The hologram lens and the diffraction grating function as the radiation angle conversion member, or as a radiation conversion member which converts the radiation direction of the secondary light.

B: For example, the light converting member 41 may be made of a resin or glass in which particles are dispersed. The particles are, for example, alumina having a high refractive index and a high reflectivity. Alternatively, for example, the light converting member 41 may be made of transparent members different in refractive index. Alternatively, for example, the light converting member 41 may be formed by a scattering plate such as frosted glass, or by a diffusion plate having minute depressions and projections provided in its surface.

C: For example, the light converting member 41 may be made of a spectrum conversion member having at least one of an optical semiconductor material, a second harmonic generation (SHG) material, and a photoluminescent material.

D, E: The light converting member 41 may be formed by a member which transmits some of the primary light and blocks the rest of the primary light.

D: This member is, for example, an optical filter. This optical filter represents, for example, at least one of a wavelength cut filter, a dye filter, and an optical resonator (etalon).

E: This member is, for example, a light transmitting modulation member. The light transmitting modulation member represents, for example, at least one of an optical switch, an electrochromic element, and a liquid crystal device.

For example, B and D are suited to the safety of the primary light source 21 and speckle removal. When the primary light source 21 emits primary light representing at least one of lamp light and LED light and the radiation angle of this primary light is adjusted, at least one of A and B can be used.

The light converting member 41 does not need to be limited to the above, and may be configured by a combination of the above.

According to the present embodiment, in the light converting member 41, the rear holding hole portions 45a, and the front holding hole portion 45b, their diameters art constant from the front to the rear. However, the present invention does not need to be limited to this as long as the secondary light is efficiently emitted from the secondary light emitting portion 43. The light converting member 41, the rear holding hole portions 45a, and the front holding hole portion 45b may have at least one of an elliptical-cone shape, an elliptical-paraboloid shape, and a partly cut elliptic shape in which the bottom surface that is in abutment with the primary light emitting portions 25 is the vertex.

Now, the second embodiment according to the present invention is described with reference to FIG. 3A, FIG. 3B, FIG. 3C, FIG. 3D, and FIG. 3E.

Figure 3A:
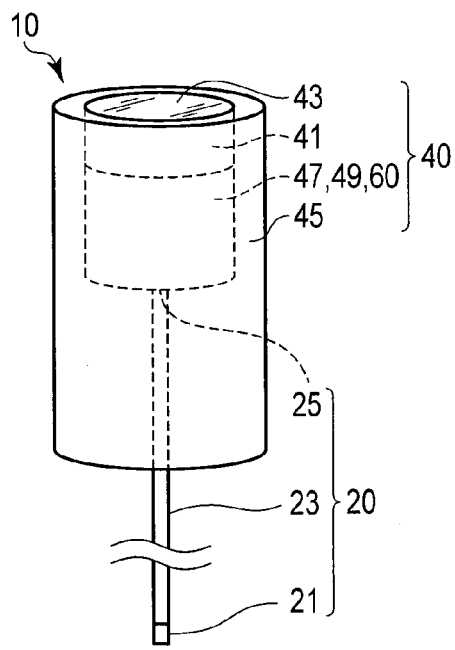
FIG. 3A is a schematic perspective view of a light source device according to a second embodiment of the present invention.
Figure 3B:
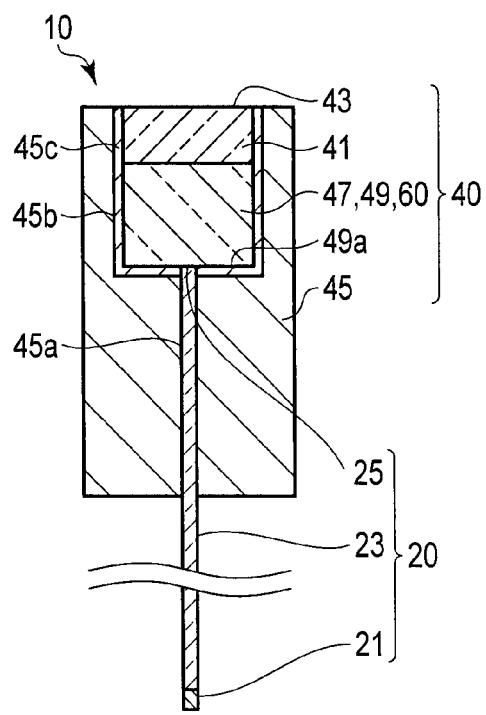
FIG. 3B is a longitudinal sectional view of the light source device shown in FIG. 3A.
Figure 3C:
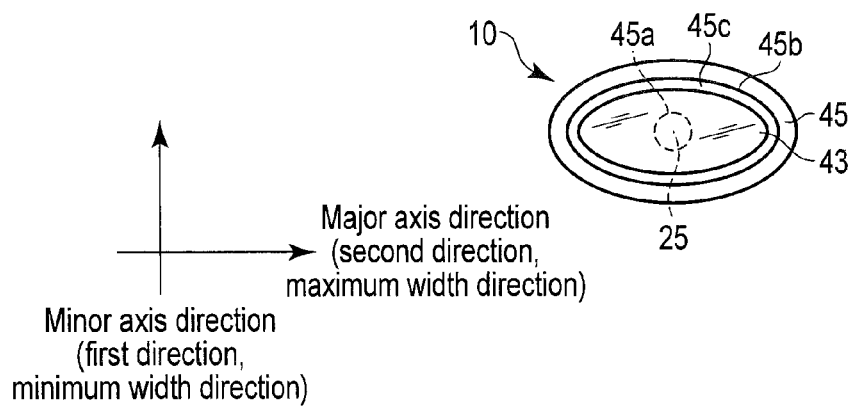
FIG. 3C is a front view of the light source device shown in FIG. 3A.
Figure 3D:
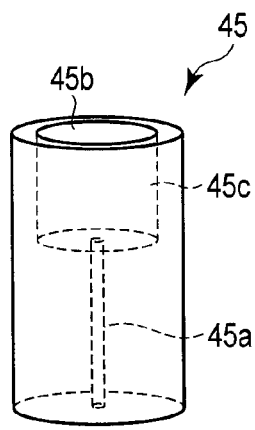
FIG. 3D is a perspective view of a holding member shown in FIG. 3A.

As shown in FIG. 3A and FIG. 3B, according to the present embodiment, in the primary light source unit 20, one primary light source 21 is provided, one optical fiber 23 is provided, and one primary light emitting portion 25 is provided.

As shown in FIG. 3A, FIG. 3B, FIG. 3C, and FIG. 3D, according to the present embodiment, in the light converting unit 40, one rear holding hole portion 45a is provided, and is provided, for example, on the central axis of the holding member 45.

As shown in FIG. 3A and FIG. 3B, the light converting unit 40 further has a transmitting member 49 which is a transmitting region 47 to transmit primary light and secondary light. The transmitting member 49 is held by the front holding hole portion 45b, and is provided between the primary light emitting portion 25 and the light converting member 41. in the optical axis direction. That is, the transmitting member 49 is provided in the rear of the light converting member 41. Thus, the light converting member 41 is mounted in the transmitting member 49.

As shown in FIG. 3A and FIG. 3B, the transmitting member 49 has the same shape as the light converting member 41, for example, an elliptic-cylinder shape. The upper surface of the transmitting member 49 has the same size as the bottom surface of the light converting member 41, and is in abutment with the bottom surface of the light converting member 41. The center of a bottom surface 49a of the transmitting member 49 is in abutment with the primary light emitting portion 25. The bottom surface 49a is formed flat. The transmitting member 49 is made of, for example, glass.

As shown in FIG. 3A and FIG. 3B, the reflecting portion 45c is provided on the inner circumferential surface and bottom surface of the front holding hole portion 45b, as in the first embodiment. Thus, the reflecting portion 45c is provided on the lateral side of the light converting member 41, on the lateral side of the transmitting member 49, and on the lower side of the transmitting member 49 except for the primary light emitting portion 25, and highly efficiently reflects the primary light and the secondary light.

Now, an operation method according to the present embodiment is described.

According to the present embodiment, since only one primary light emitting portion 25 is provided, the primary light is emitted from the primary light emitting portion 25, and is incident the transmitting member 49 so that the beam spot has a circular shape.

In this instance, the primary light with a desired light distribution travels through the transmitting member 49, and illuminates the bottom surface of the light converting member 41. The desired light distribution represents that the amount of the primary light is maximized in the normal direction of the primary light emitting portion 25, that the primary light is not inclined relative to the optical axis, and that the amount of the primary light is smaller when the inclination angle of the primary light relative to the optical axis is greater.

The inclination angle of the primary light which is emitted from the primary light emitting portion 25 toward the transmitting member 49 and which has an intensity higher than $1/e^2$ of the intensity of the primary light in the optical axis direction is defined as a critical intensity emission angle. e is Napier's constant as a base of a natural logarithm.

Thus, some of the primary light enters the transmitting member 49, and travels through the transmitting member 49 at the critical intensity emission angle. In this instance, as shown in FIG. 3E, this primary light includes primary light 77a which travels in at least the minor axis direction (minimum width direction) of the bottom surface 49a of the transmitting member 49, and primary light 77b which travels in at least the major axis direction (maximum width direction) of the bottom surface 49a of the transmitting member 49.

Figure 3E:
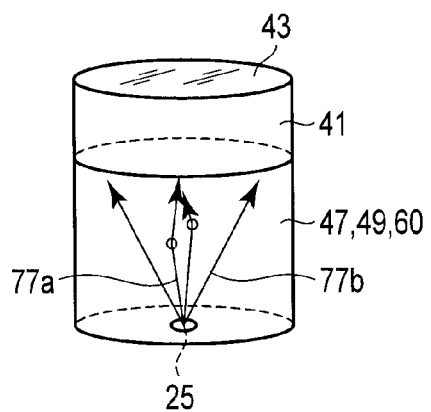
FIG. 3E is a diagram illustrating how primary light 77a and primary light 77b travel through a transmitting member.

As shown in FIG. 3E, the primary light 77a travels through the transmitting member 49 so that the primary light 77a travels from the primary light emitting portion 25 toward the reflecting portion 45c provided on the inner circumferential surface of the front holding hole portion 45b. The primary light 77a is then reflected by the reflecting portion 45c, and travels through the transmitting member 49 so that the primary light 77a travels toward the center of the bottom surface of the light converting member 41. The primary light 77a then illuminates the periphery of the center of the bottom surface of the light converting member 41.

As shown in FIG. 3E, the primary light 77b does not travel through the transmitting member 49 so that the primary light 77b travels from the primary light emitting portion 25 toward the reflecting portion 45c. The primary light 77b travels through the transmitting member 49 so that the primary light 77b travels from the primary light emitting portion 25 directly toward a position located apart from the center of the bottom surface of the light converting member 41. The primary light 77b then directly illuminates the bottom surface. In this instance, the primary light 77b illuminates the position located apart from the center of the bottom surface.

To this end, it is necessary for the transmitting member 49 to convert the shape of the beam spot of the primary light to the shape of the bottom surface of the light converting member 41 so that the diameter of the beam spot of the primary light which illuminates the bottom surface of the light converting member 41 is the same as or shorter than the major axis of the bottom surface and longer than the minor axis of the bottom surface even if the transmitting member 49 extends infinitely in a direction perpendicular to the optical axis and the reflecting portion 45c is not provided.

As a result, the primary light having a circular shape is emitted from the primary light emitting portion 25, and converted by the reflecting portion 45c and the transmitting member 49 to a state having a shape corresponding to the bottom surface of the light converting member 41 from the state having the circular shape. The primary light then illuminates the bottom surface of the light converting member 41 in this state. Thus, the reflecting portion 45c and the transmitting member 49 function as the shape converting unit 60.

The light converting member 41, the front holding hole portion 45b, and the transmitting member 49 are formed so that the above operation is possible.

Thus, according to the present embodiment, the shape of the beam spot of the primary light can be converted by the transmitting member 49 to correspond to the shape of the bottom surface of the light converting member 41 even if one optical fiber 23 is provided and one primary light emitting portion 25 is provided. Therefore, according to the present embodiment, the primary light can be applied to the entire bottom surface of the light converting member 41, and the primary light can be dispersed and applied to the entire bottom surface of the light converting member 41. Thus, according to the present embodiment, the position where heat is generated when the light converting member 41 generates secondary light can be dispersed, stronger primary light can be brought into the light converting member 41, and the secondary light can be brighter. Moreover, according to the present embodiment, the holding member 45 can be more elongate and smaller in size, so that the holding member 45 can be more easily disposed in the distal end portion 91.

Although the transmitting region 47 has the transmitting member 49 according to the present embodiment, the present invention does not need to be limited to this. The transmitting region 47 may have at least one of the transmitting member 49 and a gap portion. For example, the gap portion is formed between the light converting member 41 and the primary light emitting portion 25 when the light converting member 41 is provided apart from the primary light emitting portion 25. This gap portion is filled with, for example, air.

Now, the third embodiment according to the present invention is described with reference to FIG. 4A, FIG. 4B, FIG. 4C, and FIG. 4D.

Figure 4A:
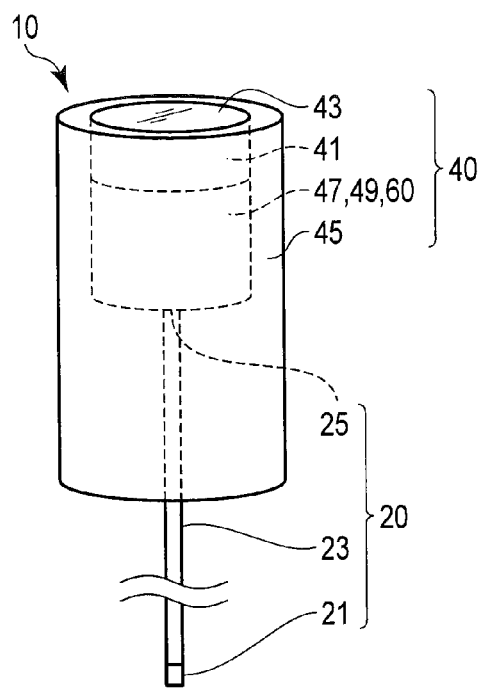
FIG. 4A is a schematic perspective view of a light source device according to a third embodiment of the present invention.
Figure 4B:
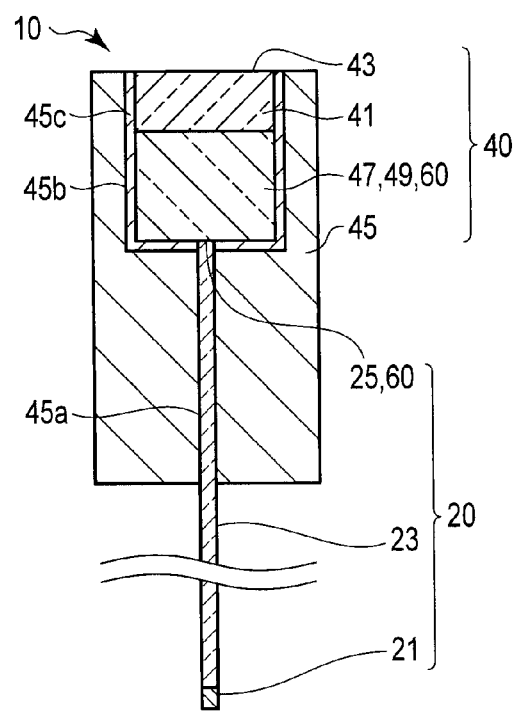
FIG. 4B is a longitudinal sectional view of the light source device shown in FIG. 4A.
Figure 4C:
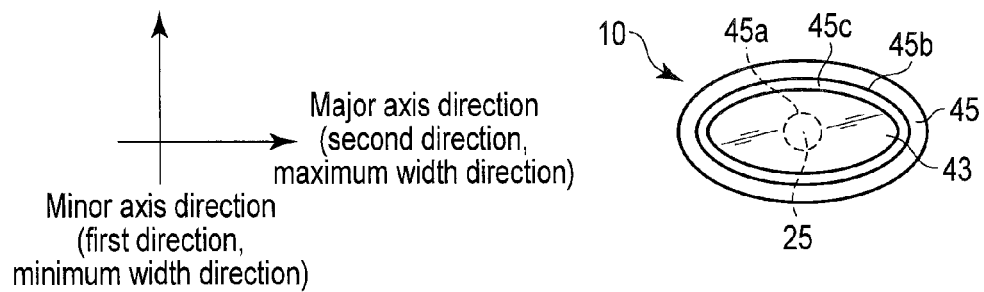
FIG. 4C is a front view of the light source device shown in FIG. 4A.
Figure 4D:
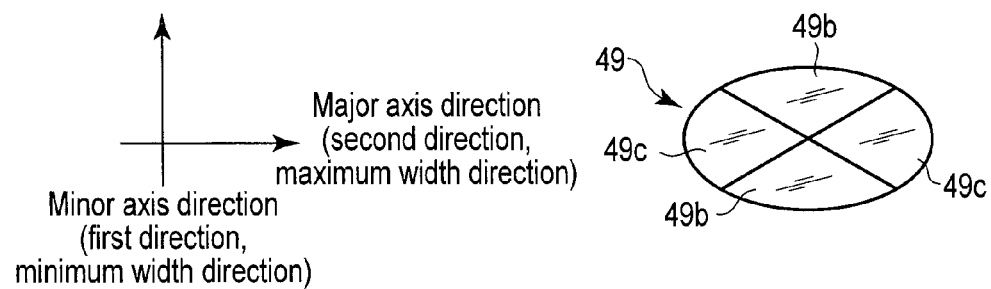
FIG. 4D is a front view of a transparent member shown in FIG. 4A.

The transmitting member 49 according to the present embodiment shown in FIG. 4A, FIG. 4B, and FIG. 4C has different refractive indexes in a plane that intersects at right angles with the optical axis of the primary light. Thus, as shown in FIG. 4D, the transmitting member 49 has high refractive regions 49b provided along the minor axis direction (minimum width direction) of the transmitting member 49, and low refractive regions 49c provided along the major axis direction (maximum width direction) of the transmitting member 49. The refractive index of the low refractive regions 49c is lower than the refractive index of the high refractive regions 49b. This transmitting member 49 is, for example, a GRIN lens. The transmitting member 49 including the high refractive regions 49b and the low refractive regions 49c is made of, for example, glass. The transmitting member 49 functions as the shape converting unit 60.

As shown in FIG. 4D, two high refractive regions 49b are provided, and two low refractive regions 49c are provided. The high refractive regions 49b and the low refractive regions 49c have, for example, a fan-shape. The high refractive regions 49b and the low refractive regions 49c are alternately provided adjacent to one another in the circumferential direction of the transmitting member 49 so that the refractive index changes by stages from the minor axis direction of the transmitting member 49 toward the major axis direction of the transmitting member 49.

According to the present embodiment, the primary light does not travel to the reflecting portion 45c, and only travels toward the bottom surface of the light converting member 41 and directly illuminates the bottom surface of the light converting member 41. The primary light travels through the low refractive region 49c at a greater angle than when passing through the high refractive region 49b.

Thus, according to the present embodiment, advantageous effects similar to those according to the second embodiment can be obtained.

According to the present embodiment, the refractive index changes by stages from the minor axis direction toward the major axis direction because of the high refractive regions 49b and the low refractive regions 49c. However, the present invention does not need to be limited to this. The refractive index may gradually change from the minor axis direction of the transmitting member 49 toward the major axis direction of the transmitting member 49.

Now, the fourth embodiment according to the present invention is described with reference to FIG. 5A, FIG. 5B, FIG. 5C, and FIG. 5D.

Figure 5A:
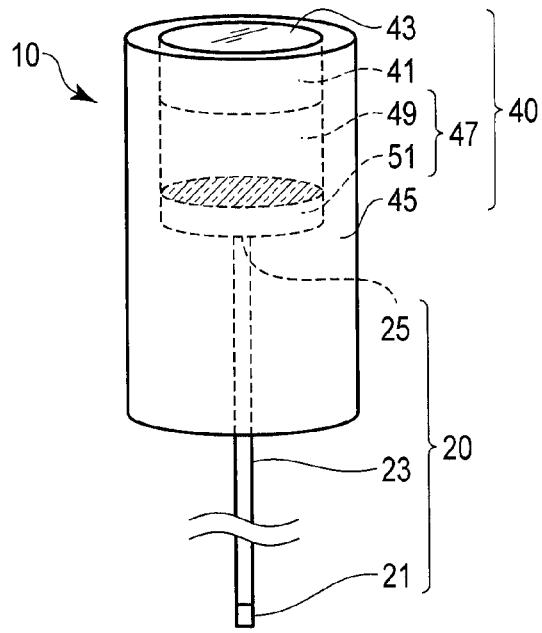
FIG. 5A is a schematic perspective view of a light source device according to a fourth embodiment of the present invention.

As shown in FIG. 5A and FIG. 5B, according to the present embodiment, the transmitting member 49 is provided apart from the primary light emitting portion 25. Thus, a gap portion 51 is provided between the transmitting member 49 and the primary light emitting portion 25. The gap portion 51 is filled with, for example, air.

According to the present embodiment, as shown in FIG. 5B and FIG. 5D, the transmitting member 49 has the bottom surface 49a which faces the primary light emitting portion 25 and which scatters the primary light in a desired one direction. The bottom surface 49a faces the primary light emitting portion 25 via the gap portion 51, and is larger than the primary light emitting portion 25. The bottom surface 49a has a rugged shape. In the bottom surface 49a, grooves 49d are provided along the minor axis direction. The shape of the grooves 49d is at least one of a wave shape, a triangular shape, and a rectangular shape. The bottom surface 49a scatters the primary light in a desired direction such as the major axis direction by the rugged shape. The transmitting member 49 illuminates the light converting member 41 in this state. The transmitting member 49 functions as the shape converting unit 60.

Thus, according to the present embodiment, advantageous effects similar to those according to the second embodiment can be obtained. Moreover, according to the present embodiment, the primary light can be applied to the light converting member 41 from various directions by the rugged bottom surface 49a.

Now, the fifth embodiment according to the present invention is described with reference to FIG. 6A, FIG. 6B, and FIG. 6C.

Figure 6A:
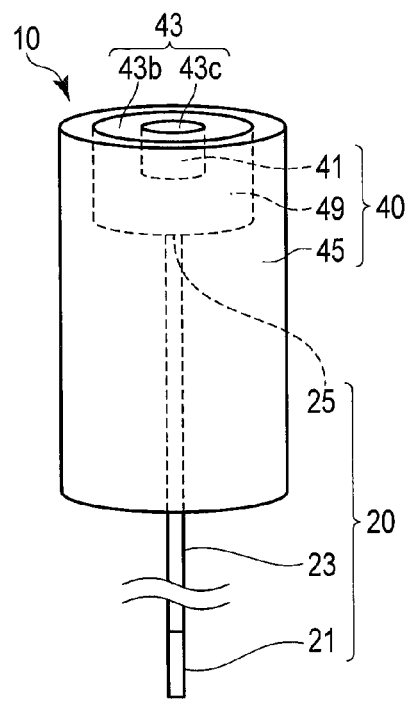
FIG. 6A is a schematic perspective view of a light source device according to a fifth embodiment of the present invention.
Figure 6B:
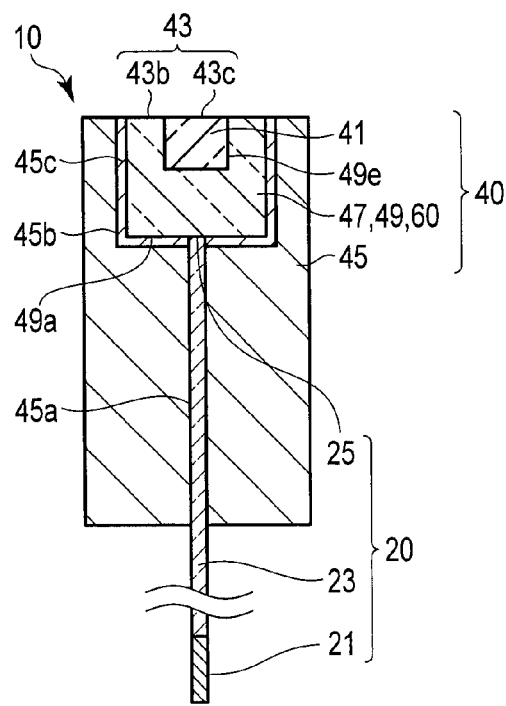
FIG. 6B is a longitudinal sectional view of the light source device shown in FIG. 6A.

As shown in FIG. 6A, FIG. 6B, and FIG. 6C, the light converting member 41 according to the present embodiment has a circular-cylinder shape, and is smaller than the front holding hole portion 45b. The light converting member 41 has the thickness that can sufficiently absorb the primary light emitted from the primary light emitting portion 25. The light converting member 41 includes, for example, a fluorescent material.

The primary light and the secondary light pass through the transmitting member 49 according to the present embodiment. This transmitting member 49 is made of, for example, transparent glass or resin which transmits visible light. The transmitting member 49 functions as the shape converting unit 60.

The transmitting member 49 has the same size as the front holding hole portion 45b, and has, for example, an elliptic-cylinder shape. Thus, the outside diameter and height of the transmitting member 49 are substantially the same as the outside diameter and height of the front holding hole portion 45b. The volume of the transmitting member 49 is substantially the same as the remainder of the volume of the front holding hole portion 45b from which the volume of the light converting member 41 is subtracted. The transmitting member 49 is fitted to or adhesively bonded to the front holding hole portion 45b. The center of the bottom surface 49a of the transmitting member 49 abuts on the primary light emitting portion 25.

The transmitting member 49 has a depression portion 49e which is provided on the upper surface side of the transmitting member 49 and to which the light converting member 41 can be fitted or adhesively bonded. The depression portion 49e has a circular-cylinder shape so that the light converting member 41 can be disposed therein. The depression portion 49e is provided on, for example, the central axis of the transmitting member 49 so that the entire primary light emitted from the primary light emitting portion 25 illuminates the bottom surface of the light converting member 41. The depression portion 49e is not penetrated through the transmitting member 49 in the axial direction of the transmitting member 49. Therefore, the light converting member 41 provided in the depression portion 49e is provided apart from the primary light emitting portion 25, and faces the primary light emitting portion 25 via the transmitting member 49. The side surface and the bottom surface of the light converting member 41 abut on the inner circumferential surface of the transmitting member 49, and the light converting member 41 is surrounded by the transmitting member 49. Thus, the transmitting member 49 surrounds the lateral side of the light converting member 41, and is provided between the primary light emitting portion 25 and the light converting member 41, and the primary light and the secondary light pass through the transmitting member 49.

The transmitting member 49 is provided so that the secondary light does not travel into the light converting member 41 but travels toward the secondary light emitting portion 43 through the transmitting member 49 when the secondary light is emitted rearward from the bottom surface of the light converting member 41 and reflected by the reflecting portion 45c.

The light converting member 41 is provided in the depression portion 49e so that the upper surface of the transmitting member 49 and the upper surface of the light converting member 41 are provided flush each other. Therefore, the upper surface of the transmitting member 49 and the upper surface of the light converting member 41 are exposed to the outside, and function as the secondary light emitting portion 43. Thus, the transmitting member 49 has one part 43b of the secondary light emitting portion 43, and the light converting member 41 has the other part 43c of the secondary light emitting portion 43. The other part 43c of the secondary light emitting portion 43 has a circular shape.

The beam spot of the primary light which is emitted from the primary light emitting portion 25 and which illuminates the bottom surface of the light converting member 41 has a circular shape. In this instance, the size of the beam spot is smaller than the bottom surface of the light converting member 41.

Now, an operation method according to the present embodiment is described.

Some of the secondary light is emitted to the outside from the upper surface of the light converting member 41 (the other part 43c of the secondary light emitting portion 43), and the rest of the secondary light is emitted to the transmitting member 49 from the side surface and the bottom surface of the light converting member 41. The rest of the secondary light travels toward the reflecting portion 45c through the transmitting member 49, and is reflected by the reflecting portion 45c in such a manner as to travel forward. The rest of the secondary light travels toward the upper surface of the transmitting member 49 through the transmitting member 49 without entering the light converting member 41 again. The rest of the secondary light is then emitted to the outside from the upper surface of the transmitting member 49 (one part 43b of the secondary light emitting portion 43).

In general, when the light converting member 41 is a fluorescent material, the light converting member 41 has an absorption property to absorb some of the secondary light (fluorescence) generated in the light converting member 41, and a scattering property to scatter the rest of the secondary light (fluorescence). In the case of the secondary light according to the present embodiment, a decrease in the amount of the secondary light caused by the absorption property and the scattering property is small. Therefore, the extraction efficiency of the secondary light is high.

In particular, the secondary light is emitted more from the bottom surface of the light converting member 41 than from the side surface of the light converting member 41. Therefore, most of the secondary light is emitted rearward. The secondary light then travels to the secondary light emitting portion 43 without passing through the fluorescent material because of the reflecting portion 45c.

Thus, according to the present embodiment, all the primary light is applied to the bottom surface of the light converting member 41 so that the secondary light can be fully generated by the light converting member 41. According to the present embodiment, the upper surface of the transmitting member 49 and the upper surface of the light converting member 41 are provided flush each other, are exposed to the outside, and function as the secondary light emitting portion 43. Therefore, according to the present embodiment, the secondary light can be fully emitted to the outside.

According to the present embodiment, the primary light emitting portion 25 and the bottom surface of the light converting member 41 are provided apart from each other due to the transmitting member 49. Therefore, according to the present embodiment, the primary light incidents the bottom surface of the light converting member 41 from the primary light emitting portion 25 in an expanded state so that the density of the primary light decreases. Thus, according to the present embodiment, local heat generation can be prevented in the bottom surface of the light converting member 41, stronger primary light can be applied to the bottom surface, and bright secondary light can be emitted.

According to the present embodiment, the bottom surface of the light converting member 41 has the same shape as the beam spot, and is larger than the beam spot. Therefore, according to the present embodiment, the secondary light emitting portion 43 having a large size can be ensured, and bright secondary light can be emitted.

According to the present embodiment, the transmitting member 49 has an elliptic-cylinder shape. Therefore, according to the present embodiment, a larger secondary light transmitting area and larger secondary light emitting portion 43 can be ensured and brighter secondary light can be emitted than when the transmitting member 49 has a circular-cylinder shape. According to the present embodiment, the secondary light can be surface-emitted to the imaging target even if the distal end face is close to the imaging target.

According to the present embodiment, the gap portion may be provided as long as the primary light emitting portion 25 and the bottom surface of the light converting member 41 are provided apart from each other.

Although one optical fiber 23, one primary light emitting portion 25, and one light converting member 41 are provided according to the present embodiment, the present invention is not limited to this. As shown in FIG. 6D, FIG. 6E, and FIG. 6F, the same number of optical fibers 23, primary light emitting portions 25, and light converting members 41 may be provided, and have only to be coaxially provided. The light converting members 41 are provided adjacent to one another, apart from one another, and linearly beside one another in the major axis direction of the transmitting member 49. The same also applies to the optical fibers 23 and the primary light emitting portions 25. Thus, according to the present embodiment, highly efficient illumination can be maintained, and the light converting unit 40 having a high aspect ratio can be provided.

The present invention is not completely limited to the embodiments described above, and modifications of components can be made at the stage of carrying out the invention without departing from the spirit thereof. Various inventions can be made by properly combining the components disclosed in the embodiments described above.

What is claimed is:

1. A light source device for a tubular observation device, the light source device comprising:
    a holding member for holding a light converting member, the holding member being separated from an outer periphery of the tubular observation device, the holding member further having a cavity for at least accommodating the light converting member,
    a primary light source unit comprising a primary light emitting portion which emits primary light, and
    a light converting unit comprising:
        the light converting member which converts the optical properties of the primary light when the primary light is applied thereto and which generates secondary light different from the primary light, and
        a secondary light emitting portion disposed on a distal end surface on an emitting side of the light converting unit, the secondary light emitting portion emitting the secondary light generated by the light converting member, the secondary light emitting portion being disposed on a distal end of the holding member inside an outer periphery of the holding member,
    wherein in a two-dimensional shape of the secondary light emitting portion projected on a surface perpendicular to an optical axis of the primary light, a length of a minimum width of the two-dimensional shape passing through a center of gravity of the two-dimensional shape is different from a length of a maximum width of the two-dimensional shape passing through the center of gravity.

2. The tubular observation device comprising the light source device according to claim 1, wherein:
    the light converting unit is incorporated in a distal end portion of the tubular observation device together with at least one functional unit,
    the holding member and the distal end faces of the at least one functional unit are provided in a layout plane representing a distal end face of the distal end portion, and
    at least part of the outline of the holding member is coincident with an edge of the layout plane.

3. The tubular observation device according to claim 2, wherein the layout plane has a layout possible region representing a region obtained when a region in which the distal end face of the at least one functional unit is disposed is removed from the layout plane,
    the secondary light emitting portion is provided in the layout possible region so that the secondary light emitting portion is exposed to the outside, and
    at least part of the outline of the holding member is coincident with part of an edge of the layout plane.

4. The tubular observation device according to claim 3, wherein the distal end face of the at least one functional unit is provided in the layout possible region so that the distal end face is exposed to the outside, and
    the layout possible region is surrounded by the edge of the layout plane and an edge of the region in which the distal end faces of the at least one functional unit is disposed.

5. The tubular observation device according to claim 4, wherein the distal end portion has a circular-cylinder shape, the layout plane has a circular shape, and part of the edge of the layout possible region has an arc shape, and
    at least part of the outline of the holding member has a shape that is coincident with part of the edge of the layout possible region.

6. The light source device according to claim 1, wherein the two-dimensional shape has one rotation symmetry axis, and the rotation symmetry axis is a twofold or more and sixfold or less rotation axis.

7. The light source device according to claim 6, wherein the two-dimensional shape has at least one of an elliptic shape, a triangular shape, a quadrangular shape, a pentangular shape, hexangular shape, a semicircular shape, and a shape at least partly having an arc or an elliptic arc, and a polygonal shape in which vertexes are formed by curves.

8. The light source device according to claim 1, further comprising a shape converting unit which converts the shape of the primary light which is emitted from the primary light emitting portion and projected on a bottom surface of the light converting member to correspond to the two-dimensional shape of the secondary light emitting portion.

9. The light source device according to claim 8, wherein the primary light emitting portion comprises two or more primary light emitting portions functioning as the shape converting unit.

10. The light source device according to claim 9, wherein the two or more primary light emitting portions are provided beside one another along the maximum width direction.

11. The light source device according to claim 8, wherein the light converting unit further comprises
a transmitting region which is provided between the primary light emitting portion and the light converting member, and having at least one of a transmitting member and a gap portion to transmit the primary light and the secondary light, and
a reflecting portion which is provided on the lateral sides of the light converting member and the transmitting region and which reflects the primary light and the secondary light,
the transmitting region and the reflecting portion function as the shape converting unit, and
when the inclination angle of the primary light which is emitted from the primary light emitting portion toward the transmitting region and which has an intensity higher than $1/e^2$ of the intensity of the primary light in the optical axis direction of the primary light is a critical intensity emission angle,
in the primary light which travels through the transmitting region at the critical intensity emission angle,
the primary light which travels in at least the minimum width direction travels through the transmitting region so that the primary light travels toward the reflecting portion, reflected by the reflecting portion, and directly illuminates the light converting member, and
the primary light which travels in at least the maximum width direction travels through the transmitting region and then directly illuminates the light converting member.

12. The light source device according to claim 8, wherein the light converting unit further comprises
a transmitting member which is provided between the primary light emitting portion and the light converting member and which transmits the primary light and the secondary light and which functions as the shape converting unit,
wherein the transmitting member has a first area and a second area, the second area having a different refractive index from a refractive index of the first area in a plane that intersects at right angles with the optical axis of the primary light.

13. The light source device according to claim 12, wherein the transmitting member has high refractive regions provided along the minimum width direction, and low refractive regions which are provided along the maximum width direction, the low refractive regions having a refractive index lower than the refractive index of the high refractive regions.

14. The light source device according to claim 13, wherein the high refractive regions comprise two high refractive regions, and the low refractive regions comprise two low refractive regions, and
the two high refractive regions and the two low refractive regions are alternately provided adjacent to one another in the circumferential direction of the transmitting member so that the refractive index changes by stages from the minimum width direction toward the maximum width direction.

15. The light source device according to claim 13, wherein the refractive index gradually changes from the minimum width direction toward the maximum width direction.

16. The light source device according to claim 8, wherein the light converting unit further comprises
a transmitting member which is provided between the primary light emitting portion and the light converting member and apart from the primary light emitting portion and which transmits the primary light and the secondary light and which functions as the shape converting unit, and
the transmitting member has a surface which faces the primary light emitting portion and which scatters the primary light in a desired one direction.

17. The light source device according to claim 1, wherein the light converting unit further comprises
a transmitting member which surrounds the lateral side of the light converting member and which is provided between the primary light emitting portion and the light converting member and which transmits the primary light and the secondary light,
the transmitting member has one part of the secondary light emitting portion, and the light converting member has the other part of the secondary light emitting portion, and
the other part of the secondary light emitting portion has a circular shape.

18. The light source device according to claim 17, wherein the light converting member comprises two or more light converting members, and the primary light emitting portion comprises a same number of primary light emitting portions as the two or more light converting members.

19. The light source device according to claim 18, wherein the two or more light converting members are linearly provided beside one another along the maximum width direction.

20. The light source device according to claim 1, wherein the secondary light emitting portion comprises a distal end face of the light converting member.

21. The light source device according to claim 1, wherein a shape of a distal end surface of the light converting member is coincident with a shape of the secondary light emitting portion.

22. The light source device according to claim 1, wherein:
the light converting unit comprises a plurality of light converting members, and
an optical function of each of the plurality of light converting members is substantially the same.

23. The light source device according to claim 1, wherein:
the light converting unit comprises a plurality of light converting units;
an optical function of each of the plurality of light converting units is substantially the same; and
the secondary light emitting portion of each of the plurality of light converting units is independent from each other.

24. The light source device according to claim 23, wherein the secondary light emitting portion disposed in one of the plurality of light converting units is disposed symmetrically to the secondary light emitting portion disposed in another of the plurality of light converting units.

25. The light source device according to claim 1, wherein the secondary light emitting portion has at least one of an elliptic shape, a triangular shape, a quadrangular shape, a pentangular shape, a hexangular shape, a semicircular shape, and a polygonal shape in which vertexes are formed by curves.

26. The light source device according to claim 1, wherein the primary light source unit further comprises a light guide member for guiding the primary light to the light converting unit.

27. The light source device according to claim 26, wherein the holding member includes a bore for accommodating the light guide member, the bore being in optical communication with the cavity.

* * * * *